(12) United States Patent
Mizumoto (10) Patent No.: US 11,628,098 B2
(45) Date of Patent: Apr. 18, 2023

(54) ABSORBENT ARTICLE

(71) Applicant: DAIO PAPER CORPORATION, Ehime (JP)

(72) Inventor: Yousei Mizumoto, Tochigi (JP)

(73) Assignee: DAIO PAPER CORPORATION, Ehime (JP)

(*) Notice: Subject to any disclaimer, the term of this patent is extended or adjusted under 35 U.S.C. 154(b) by 193 days.

(21) Appl. No.: 17/047,215

(22) PCT Filed: May 21, 2019

(86) PCT No.: PCT/JP2019/020150
§ 371 (c)(1),
(2) Date: Oct. 13, 2020

(87) PCT Pub. No.: WO2019/235215
PCT Pub. Date: Dec. 12, 2019

(65) Prior Publication Data
US 2021/0161730 A1 Jun. 3, 2021

(30) Foreign Application Priority Data
Jun. 4, 2018 (JP) .............................. JP2018-106939

(51) Int. Cl.
*A61F 13/475* (2006.01)
*A61F 13/534* (2006.01)
(Continued)

(52) U.S. Cl.
CPC ........ *A61F 13/4756* (2013.01); *A61F 13/534* (2013.01); *A61F 13/535* (2013.01);
(Continued)

(58) Field of Classification Search
CPC ........ A61F 13/4756; A61F 2013/15357; A61F 13/15203; A61F 13/4702; A61F 13/4704; A61F 2013/4587
See application file for complete search history.

(56) References Cited

U.S. PATENT DOCUMENTS 5,846,231 A    12/1998   Fujioka et al.
2005/0148972 A1*  7/2005   Miyama ............ A61F 13/47218
                                                604/385.04
(Continued)

FOREIGN PATENT DOCUMENTS

JP   H06-009616 U    2/1994
JP   2007-144104     6/2007
(Continued)

OTHER PUBLICATIONS

International Search Report for PCT/JP2019/020150 dated Jul. 16, 2019.
(Continued)

*Primary Examiner* — Susan S Su
*Assistant Examiner* — Ted Yang
(74) *Attorney, Agent, or Firm* — IPUSA, PLLC (57) ABSTRACT

An absorbent article includes a liquid permeable top sheet, a liquid impermeable back sheet, and an absorber provided between the two sheets, the absorbent article having a predetermined length in a front-to-rear direction, and a predetermined width in a width direction perpendicular to the front-to-rear direction, wherein the absorber is provided with a groove or a slit extending in the front-to-rear direction, the absorber includes a first absorber layer on the side closer to the top sheet, and a second absorber layer on the side closer to the back sheet, and the first absorber layer includes a high-stiffness part extending outward in the width direction from an edge portion of the groove or slit, and a (Continued)

stiffness of the high-stiffness part is higher than a stiffness of the second absorber layer.

20 Claims, 7 Drawing Sheets

(51) Int. Cl.
    *A61F 13/535* (2006.01)
    *A61F 13/15* (2006.01)
(52) U.S. Cl.
    CPC ............... *A61F 2013/15357* (2013.01); *A61F 2013/15439* (2013.01)

(56) References Cited

U.S. PATENT DOCUMENTS

| | | | | |
|---|---|---|---|---|
| 2005/0182374 A1* | 8/2005 | Zander | ................... | A61F 13/533 604/380 |
| 2012/0109096 A1* | 5/2012 | Burvall | ............... | A61F 13/4702 604/385.31 |
| 2018/0042783 A1* | 2/2018 | Coffman | ............. | A61F 13/4756 |
| 2018/0338872 A1 | 11/2018 | Takahashi | | |
| 2018/0344541 A1 | 12/2018 | Ito et al. | | |

FOREIGN PATENT DOCUMENTS

| | | | | |
|---|---|---|---|---|
| JP | 2007-144105 | 6/2007 | | |
| JP | 2012-115378 | 6/2012 | | |
| JP | 6068126 | 1/2017 | | |
| JP | 2017-047147 | 3/2017 | | |
| JP | 2017-064134 | 4/2017 | | |
| JP | 2017-136273 | 8/2017 | | |
| WO | 2016/114209 | 7/2016 | | |
| WO | WO-2016114209 A1 * | 7/2016 | ........... | A61F 13/535 |
| WO | 2017/051695 | 3/2017 | | |
| WO | 2017/135022 | 8/2017 | | |

OTHER PUBLICATIONS

Extended European Search Report for 19816063.2 dated Aug. 13, 2021.

* cited by examiner

ABSORBENT ARTICLE

TECHNICAL FIELD

The present invention relates to an absorbent article.

BACKGROUND ART

As absorbent articles, disposable diapers in the form of pad type, tape type, pants type, or the like, as well as sanitary napkins, are known. Typically, such an absorbent article includes a liquid permeable top sheet, a liquid impermeable back sheet, and an absorber provided between the two sheets.

In the above described absorbent articles, there is a known structure provided with a groove or slit extending in a front-to-rear direction of the absorber. Such a groove or slit acts to promote transfer of body fluid in the front-to-rear direction and prevent a leak in a width direction, to improve air permeability, or the like. For example, Patent Document 1 describes an absorber having a recessed part 13 extending in a longitudinal direction Y.

PRIOR ART DOCUMENTS

Patent Document

Patent Document 1: Japanese Patent No. 6068126

DISCLOSURE OF THE INVENTION

Problem to be Solved by the Invention

In a case where body pressure is applied in a thickness direction of the absorber, the absorber may expand in a plane direction, and cause the groove or slit to close (collapse) and deteriorate the function thereof. However, Patent Document 1 does not refer to the collapse of the recess (groove).

In view of the foregoing, one object according to one aspect of the present invention is to provide an absorbent article in which the groove or the like formed in the absorber is unlikely to collapse, and the flexibility of the absorber can be secured.

Means for Solving the Problem

According to one aspect of the present invention, an absorbent article includes a liquid permeable top sheet, a liquid impermeable back sheet, and an absorber provided between the two sheets, the absorbent article having a predetermined length in a front-to-rear direction, and a predetermined width in a width direction perpendicular to the front-to-rear direction, wherein the absorber is provided with a groove or a slit extending in the front-to-rear direction, the absorber includes a first absorber layer on the side closer to the top sheet, and a second absorber layer on the side closer to the back sheet, and the first absorber layer includes a high-stiffness part extending outward in the width direction from an edge portion of the groove or slit, and a stiffness of the high-stiffness part is higher than a stiffness of the second absorber layer.

Effects of the Invention

According to one aspect of the present invention, it is possible to provide an absorbent article in which the groove or the like formed in the absorber is unlikely to collapse, and the flexibility of the absorber can be secured.

MODE OF CARRYING OUT THE INVENTION

Hereinafter, embodiments of the present invention will be described with reference to the drawings. In each of the drawings, unless otherwise indicated, the same or corresponding structures will be designated by the same reference numerals, and a description thereof may be omitted.

Figure 1:
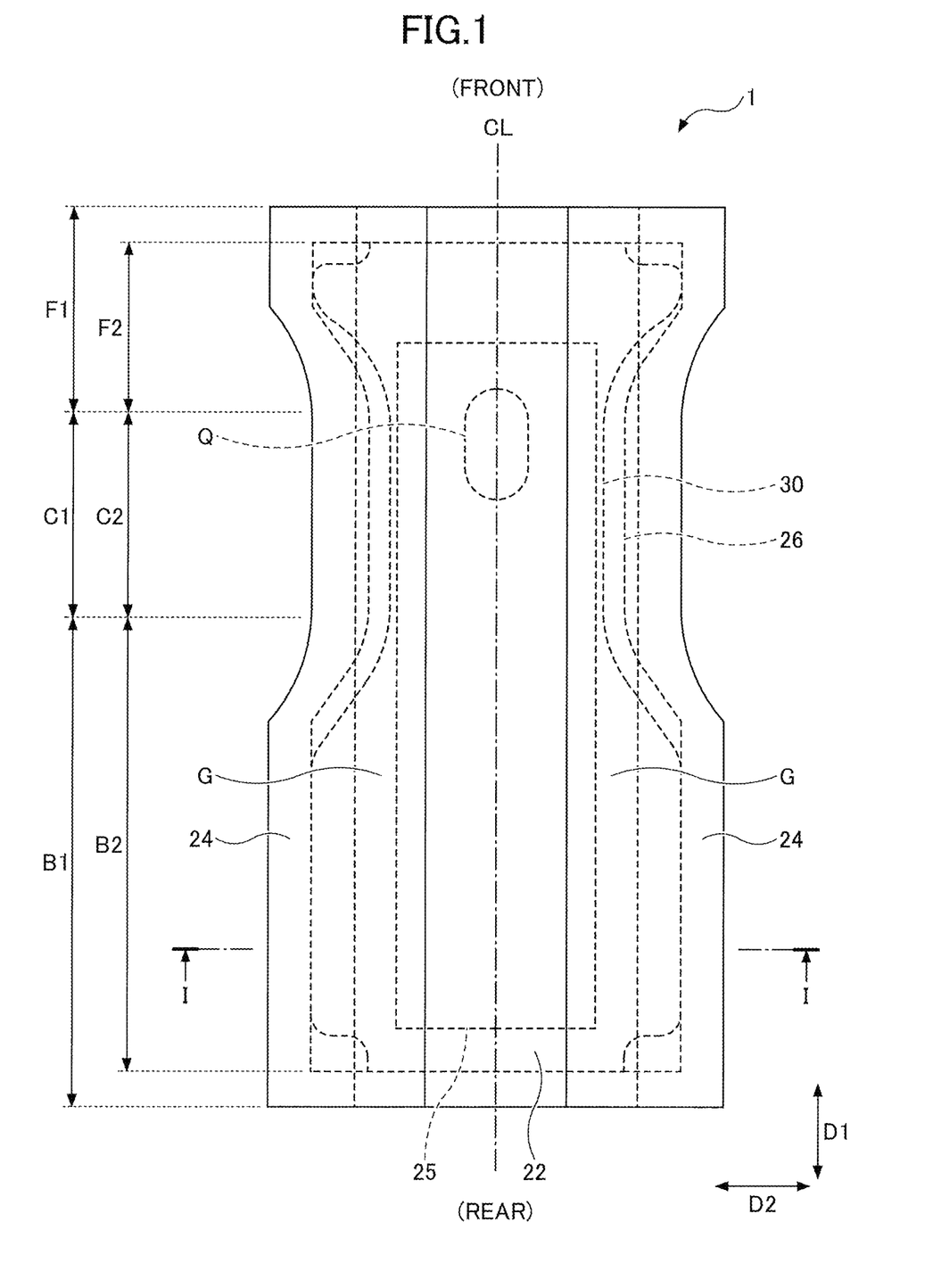
FIG. 1 is a plan view of an absorbent article according to one embodiment of the present invention.
Figure 2:
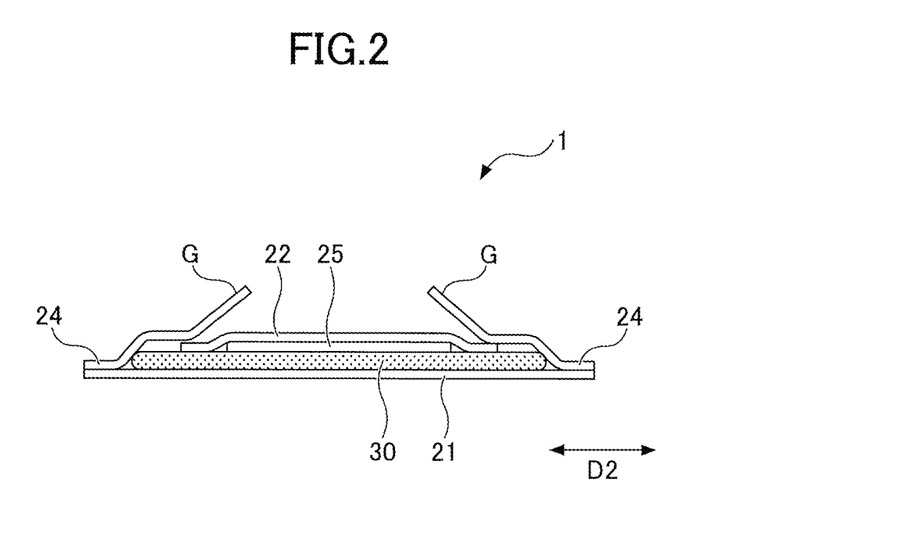
FIG. 2 is a cross sectional view along a line I-I in FIG. 1.

First, a basic structure of an absorbent article according to one embodiment of the present invention will be described with reference to FIG. 1 and FIG. 2. FIG. 1 illustrates a top view of an absorbent article 1, and FIG. 2 illustrates a cross sectional view along a line I-I in FIG. 1. According to this embodiment, a pad type disposable diaper (incontinence pad) will be described as an example.

As illustrated in FIG. 1 and FIG. 2, the absorbent article 1 includes a liquid permeable top sheet 22, a liquid impermeable back sheet 21, and an absorber 30 provided between the two sheets 21 and 22. As will be described later, the absorber 30 may be formed by a plurality of layers including a first (top or upper) absorber layer on the side closer to the top sheet 22, and a second (bottom or lower) absorber layer on the side closer to the back sheet 21. When the absorbent article 1 is worn, the side closer to the top sheet 22 becomes the skin side, and the side closer to the back sheet 21 is fixed to an outer (outer diaper), underwear, or the like.

According to this embodiment, the absorbent article 1 as a whole has an elongated shape in a plan view. In other words, the absorbent article 1 has a predetermined length in a first direction (front-to-rear direction or longitudinal direction) D1, and has a predetermined width in a second direction (width direction) D2 that is perpendicular to the first direction D1 and is smaller than the above described length. Front and rear portions of the absorbent article 1 correspond to the ventral and dorsal portions when worn, respectively.

According to the embodiment illustrated in FIG. 1 and FIG. 2, the shape of the absorbent article 1 in the plan view is line symmetrical with respect to a center line CL in the front-to-rear direction, however, the planar shape does not necessarily have to be line symmetrical. In addition, the shape of the absorbent article 1 in the plan view does not necessarily have to include a portion (constricted portion) having a narrower width compared to the front and rear regions thereof as described above, and may have other shapes, such as a rectangular shape or the like having a constant width along the front-to-rear direction D1.

Moreover, although the structure (material, arrangement, or the like of each constituent element) of the absorbent article 1, other than the shape, is line symmetrical with respect to the center line CL in the front-to-rear direction, the structure does not necessarily have to be line symmetrical.

As illustrated in FIG. 1, the absorbent article 1 has a crotch corresponding region C1 near a center thereof when viewed in the front-to-rear direction D1. In this specification, the "crotch corresponding region" refers to a portion corresponding to a wearer's crotch (inseam) when the absorbent article is worn. For example, the crotch corresponding region C1 may be in a range from the center or a vicinity thereof in the front-to-rear direction to a predetermined front position of the absorbent article, or in a predetermined range from the center in the front-to-rear direction of the absorbent article. According to the embodiment illustrated in FIG. 1 and FIG. 2, the constricted portion having the narrower width is formed in the absorbent article 1, and a portion of the region where the constricted portion is formed becomes the crotch corresponding region. Further, a region adjacent to and in front of the crotch corresponding region C1, and extending to a front end of the absorbent article 1, forms a front region F1, and a region adjacent to and to the rear of the crotch corresponding region C1, and extending to a rear end of the absorbent article 1, forms a rear region B1. In this specification, the rear region B1 corresponds to buttocks of the wearer when the absorbent article is worn, and is also referred to as a "buttocks corresponding region".

A body fluid excretion orifice corresponding portion Q, corresponding to a body fluid excretion orifice of the wearer when the absorbent article 1 is worn, may be positioned on the center line CL in the front-to-rear direction of the absorbent article 1. This body fluid excretion orifice corresponding portion Q may be positioned in the crotch corresponding region C1, or may be positioned to extend from the crotch corresponding region C1 toward the front region F1, as illustrated in FIG. 1.

An overall length (length along the front-to-rear direction D1) of absorbent article 1 may be approximately 350 mm to approximately 700 mm, and an overall width (length along the width direction D2) may be approximately 130 mm to approximately 400 mm. In addition, a length of the crotch corresponding region C1 along the front-to-rear direction D1 may be approximately 10 mm to approximately 150 mm, a length of the front region F1 along the front-to-rear direction D1 may be approximately 50 mm to approximately 350 mm, and a length of the rear region B1 along the front-to-rear direction D1 may be approximately 50 mm to approximately 350 mm. Moreover, in the case where the absorbent article 1 includes the constricted portion, a minimum width thereof is preferably approximately 50% to approximately 90% of the overall width of the absorbent article 1 (the length along the width direction D2 before and after the constricted portion).

As illustrated in FIG. 1, the size of the back sheet 21 may be greater than the size of the absorber 30. In this case, the absorber 30 can be arranged within a range of the back sheet 21. The liquid impermeable back sheet 21 may be a polyethylene film or the like, or a sheet having a moisture permeability without deteriorating the liquid impermeability from a viewpoint of preventing mustiness caused by moisture. The liquid impermeable and moisture permeable sheet may be a micro-porous sheet that is obtained by melting and kneading an inorganic filler material in an olefin resin, such as polyethylene, polypropylene, or the like, for example, to form a sheet, and stretching the sheet along a uniaxial direction or biaxial directions. An outer surface of the back sheet 21 may be covered by an outer sheet, such as a nonwoven fabric or the like.

According to the embodiment illustrated in FIG. 2, the top sheet 22 does not cover portions at ends of the absorber 30 along the width direction D2, however, the top sheet 22 may cover the entire absorber 30. Perforated or non-perforated nonwoven fabrics, perforated plastic sheets, or the like may be used as the top sheet 22. In addition to synthetic fibers such as olefin-based fibers including polyethylene, polypropylene, or the like, polyester-based fibers, amide-based fibers, or the like, recycled fibers such as rayon, cupra, or the like, and natural fibers such as cotton or the like, may be used as a fiber material forming the nonwoven fabric.

As illustrated in FIG. 1 and FIG. 2, an intermediate sheet 25 may be interposed between the top sheet 22 and the absorber 30. By providing the intermediate sheet 25, it is possible to prevent reversal of a body fluid absorbed by the absorber 30. For this reason, a material having a low water retention and a high liquid permeability, such as various nonwoven fabrics, mesh films, or the like, is preferably used for the intermediate sheet 25.

The back sheet 21 and the top sheet 22 are bonded together at both ends of the absorber 30 along the front-to-rear direction D1. In addition, the back sheet 21, and gather sheets 24 and 24 provided along the front-to-rear direction D1 on both side portions of the absorbent article 1, are bonded together at both side portions of the absorbent article 1 along the width direction D2.

Plastic sheets, meltblown nonwoven fabrics, or the like may be used for the gather sheets 24, however, from a viewpoint of providing an excellent feeling upon touching the skin, the nonwoven fabric is preferably subjected to a water repellent treatment using silicone or the like.

As illustrated in FIG. 1 and FIG. 2, each of the gather sheets 24 and 24 is provided in an overlapping manner on the top sheet 22. In addition, an elastic member, that is fixed in an elongated state along the front-to-rear direction, may be provided at the end on the inner side of each gather sheet 24 along the width direction D2. This elastic member may be manufactured from styrene-based rubbers, olefin-based rubbers, urethane-based rubbers, ester-based rubbers, or the like that are formed into a thread-like shape, a string-like shape, a band-like shape, or the like.

Moreover, the gather sheet 24 may be bonded to the top sheet 22, a packaging sheet 26, or the back sheet 21 that is arranged immediately underneath, at the front and rear ends and side edges thereof. As described above, if the elastic member is provided at the end on the inner side of each gather sheet 24 along the width direction D2, non-bonded portions of the gather sheets 24 (that is, regions on the inner side along the width direction D2, and excluding both ends thereof) can form gathers G and G standing on the front side (on the side closer to the top sheet 22) of the absorbent article 1 (FIG. 2). The gathers G and G can prevent a leak or the like of the body fluid to the side. The gather sheets 24 and 24 and the constituent elements underneath may be bonded using a hot-melt adhesive, heat-sealing, or ultrasonic sealing, for example.

The absorber 30 includes a crotch corresponding region C2 near the center thereof when viewed in the front-to-rear direction D1, and this crotch corresponding region C2 corresponds to the crotch corresponding region C1 of the absorbent article 1 described above. Further, a region adjacent to and in front of the crotch corresponding region C2, and extending to a front end of the absorber 30, forms a front region F2, and a region adjacent to and to the rear of the crotch corresponding region C2, and extending to a rear end of the absorber 30, forms a rear region B2.

The shape of the absorber 30 in the plan view includes a constricted portion, similar to the planar shape of the entire absorbent article 1, but may have a rectangular shape or the like having a constant width along the front-to-rear direction D1 and not including the constricted portion, regardless of the planar shape of the absorbent article 1. In a case where the absorber 30 includes the constricted portion as in accordance with the embodiment illustrated in FIG. 1, a minimum width of the constricted portion may be approximately 50% to approximately 75% of the length of the front and rear regions of the constricted portion along the width direction D2. In addition, in the case where the absorber 30 includes the constricted portion, the crotch corresponding region C2, that includes at least a portion of the constricted portion, may be arranged in a front half region of the absorber 30 as illustrated in FIG. 1, or may be arranged at the center of the absorber 30 along the front-to-rear direction D1, depending on the overall structure of the absorbent article.

A material included in the absorber 30 may include a fiber pile of pulp fibers, a bulk material of filaments made of cellulose acetate or the like, a nonwoven fabric, or the like, and further, a superabsorbent polymer in particulate form or the like may be mixed, adhered, or the like, and used as the material, as appropriate. In addition, the absorber material may also include superabsorbent polymer fibers, polymer particles other than the high-absorbance polymer particles, inorganic particles, or the like.

The mass per unit area of the fiber, and the mass per unit area of the superabsorbent polymer, in the absorber 30, may be determined appropriately. In the absorber 30 as a whole, the mass per unit area of the fiber is preferably set in a range of approximately 100 g/m$^2$ to approximately 700 g/m$^2$, and the mass per unit area of the superabsorbent polymer is preferably set in a range of approximately 50 g/m$^2$ to approximately 550 g/m$^2$.

The absorber 30 is preferably wrapped in the packaging sheet 26 (FIG. 1), such as a nonwoven fabric, crepe paper, or the like. In the case where the absorber 30 includes the particulate material such as the polymer particles or the like, it is particularly preferable to use the packaging sheet 26 that can include a spill of the material.

The entire absorber 30 may be wrapped in the packaging sheet 26 described above. In addition, as will be described later, in a case where the absorber 30 is formed by a plurality of layers including a first absorber layer 31 and a second absorber layer 32, each absorber layer may be wrapped in the packaging sheet, or the packaging sheet may be sandwiched between the absorber layers. Moreover, the packaging sheet may be non-colored (that is, white), or may be colored. The coloring may be in a color that can make the color of the excreted body fluid less conspicuous, such as a color that is close to the color of the body fluid, or a complementary color to the color of the body fluid or a color close to the complementary color, for example.

Next, the structure of the absorber of the above described absorbent article will be described in more detail. According to one embodiment of the present invention, the absorber may include the plurality of layers. More particularly, the absorber has a laminated structure that includes the first absorber layer on the side closer to the top sheet 22, and the second absorber layer on the side closer to the back sheet. Because the absorber includes the plurality of layers, it is possible to make each of the layers perform a different function.

Figure 3:
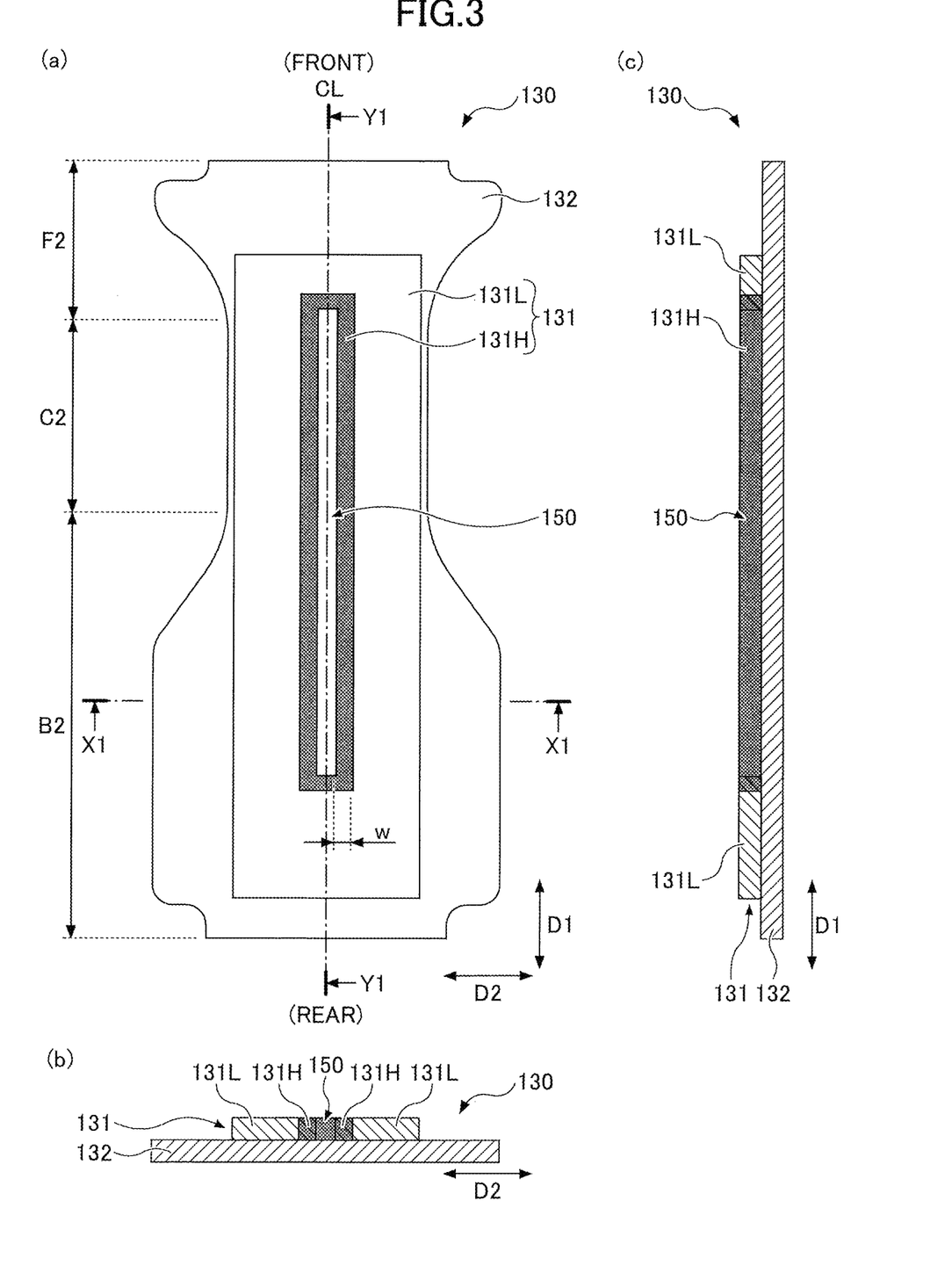
FIG. 3 is a diagram illustrating an absorber according to a first embodiment of the present invention.

FIG. 3 illustrates an absorber 130 according to a first embodiment of the present invention. FIG. 3(*a*) illustrates a top view (viewed from the side closer to the top sheet) of the absorber 130, FIG. 3(*b*) illustrates a cross sectional view of along a line X1-X1 in FIG. 3(*a*), and FIG. 3(*c*) illustrates a cross sectional view along a line Y1-Y1 in FIG. 3(*a*).

As illustrated in FIG. 3(*a*) through FIG. 3(*c*), the absorber 130 includes a first absorber layer 131 on the side (the upper side) closer to the top sheet, and a second absorber layer 132 laminated under the first absorber layer 131. Because the absorber 130 includes the two layers, namely, the first absorber layer 131 and the second absorber layer 132, it is possible to make each of the layers perform a different function. Alternatively, even when each of the layers performs the same function, the degree of the function may be varied among the layers.

According to the embodiment illustrated in FIG. 3, the first absorber layer 131 is arranged at the center along the width direction D2, and extends from a position exceeding the front end of the crotch corresponding region C2 along the front-to-rear direction D1, to a position exceeding the center of the rear region B2 along the front-to-rear direction D1. Accordingly, an amount of absorption of the absorber 130 can be increased at the body fluid excretion orifice corresponding portion Q (FIG. 1) and the vicinity thereof, and in a region to which the body fluid from the body fluid excretion orifice corresponding portion Q may easily diffuse and permeate.

The shape of the first absorber layer 131 is a rectangular shape having an approximately constant width, and a length elongated in the front-to-rear direction D1, and the shape of the second absorber layer 132 includes a constricted portion along the shape of the absorbent article. In addition, the size of the lower second absorber layer 132 is greater than the size of the upper first absorber layer 131, that is, the upper first absorber layer 131 has the size so as not to protrude from the lower second absorber layer 132. The width of the first absorber layer 131 is slightly smaller than the width of the second absorber layer 132 in the crotch corresponding region C2, and is approximately one-half the width of the second absorber layer 132 in the rear region (buttocks corresponding region) B2. However, a relationship between the region where the first absorber layer 131 is provided and the region where the second absorber layer 132 is provided is not limited to that illustrated in FIG. 3, and the planar shapes and/or sizes of the first absorber layer 131 and the second absorber layer 132 that are laminated may be the same.

The absorber 130 is provided with a groove 150 extending in the front-to-rear direction D1. As illustrated in FIG. 3(*a*), the groove 150 extends from the position exceeding the front end of the crotch corresponding region C2 to the position exceeding the center of the rear region B2 along the front-to-rear direction D1, however, the structure of the groove provided in the absorber is not limited to that illustrated in FIG. 3, and may include various structures including those illustrated in the embodiments described later.

Because the presence of the grooves 150 enables quick transfer of the body fluid in the front-to-rear direction D1 along the grooves 150, the leak in the width direction D2 can be prevented even when a large amount of the body fluid is excreted at one time. In addition, the presence of the groove 150 can also improve the air permeability of the absorbent article.

The width of the groove 150 may be approximately 10 mm to approximately 30 mm. The width of the groove 150 does not necessarily have to be constant along the front-to-rear direction D1, and may vary. In addition, the length of the groove 150 may be 100 mm to 350 mm. According to the embodiment illustrated in FIG. 3, a single groove 150 that is continuous along the front-to-rear direction D1 is provided, however, the groove may be divided into a plurality of grooves in the front-to-rear direction D1. Moreover, a plurality of grooves, spaced apart in the width direction D2, may be provided.

In the upper first absorber layer 131, a high-stiffness part 131H extends from an edge to an outer side of the groove 150 along the width direction D2, as illustrated in FIG. 3(a) and FIG. 3(b). The high-stiffness part 131H is a portion having a stiffness that is relatively higher than that of the adjacent absorber. The stiffness of the high-stiffness part 131H is higher than the stiffness of the second absorber layer laminated underneath. The stiffness of the high-stiffness part 131H is higher than the stiffness of the portion adjacent to the outer side of the high-stiffness part 131H along the width direction D2. In the first absorber layer 131, a portion (according to this embodiment, a portion of the absorber adjacent to the outer side of the high-stiffness part 131H along the width direction D2) having a stiffness lower than that of the high-stiffness part 131H, will be referred to as a low-stiffness part 131L.

The stiffnesses of the high-stiffness part 131H and the low-stiffness part 131L in the first absorber layer 131 may be uniform or varied within each portion. In addition, the stiffness of the second absorber layer 132 may be uniform or varied within the layer.

The absorbent article may be deformed upon receiving various forces while being worn (used). For example, in a case where the absorbent article is pushed in the thickness direction by the wearer's buttocks, the absorber may be crushed in the thickness direction and expand in the width direction D2 and the front-to-rear direction D1. Accordingly, in the case where the groove extends in the front-to-rear direction D1 as in accordance with this embodiment, the edges of the groove may approach each other in the width direction D2, thereby narrowing the width of the groove, or closing the groove.

On the other hand, when the high-stiffness part 131H, extending in the width direction from the edge of the groove 150, is formed in the absorber 130 as described above, the high-stiffness part 131H is unlikely to be deformed even when a force is applied to the absorber 130. Hence, it is possible to reduce the width of the groove 150 from narrowing or closing (also referred to as "collapsing of the groove"). Accordingly, it is possible to maintain the original functions of the groove 150, that is, to improve guiding of the body fluid and improve the air permeability. In other words, the groove 150 is reinforced by the high-stiffness part 131H.

As described above, the stiffness of the high-stiffness part 131H is higher than the stiffness of the second absorber layer 132 laminated underneath. In other words, the second absorber layer having the lower stiffness is provided on the side (the lower side) of the high-stiffness part 131H closer to the back sheet. For this reason, it is possible to obtain the flexibility of the absorber by the lower second absorber layer 132, while securing the above described effect of the high-stiffness part 131H that avoids the collapsing of the groove (making it unlikely for the groove to collapse).

As illustrated in FIG. 3(a), the high-stiffness part 131H is provided continuously along the groove 150 and in the front-to-rear direction D1 in the top view. However, as long as the effect of preventing the groove from collapsing does not deteriorate, the high-stiffness part 131H may include a discontinuous portion. In addition, the high-stiffness part 131H that is configured to reinforce the groove 150, may be provided particularly in a region where the groove is to be prevented from collapsing, and not provided in other regions. For example, the reinforcement by the high-stiffness part 131H may be provided mainly in the buttocks corresponding region B2 where the force in the thickness direction may easily be applied, but not provided in the crotch corresponding region C2 and the front region F2 in front of the buttocks corresponding region B2. According to such a structure in which the high-stiffness part is concentrated in the region where the groove may easily collapse, it is possible to effectively prevent the groove from collapsing, using a relatively small amount of the high-stiffness part 131H, that is, the high-stiffness part 131H including a relatively small amount of the absorber. In addition, it is possible to improve the flexibility in the regions other than the region where the groove is to be particularly prevented from collapsing.

Moreover, according to this embodiment, the high-stiffness part 131H also extends from the front and rear ends of the grooves 150 in the front-to-rear direction D1. This embodiment is preferable in that the groove can easily maintain the original shape of the groove even when the absorber receives a force from the side or the like. Accordingly, from a viewpoint of preventing the groove from collapsing and maintaining the function of the groove, the high-stiffness part 131H is preferably provided continuously to surround the entire groove 150 (to border the groove 150), as illustrated in FIG. 3(a).

Figure 6:
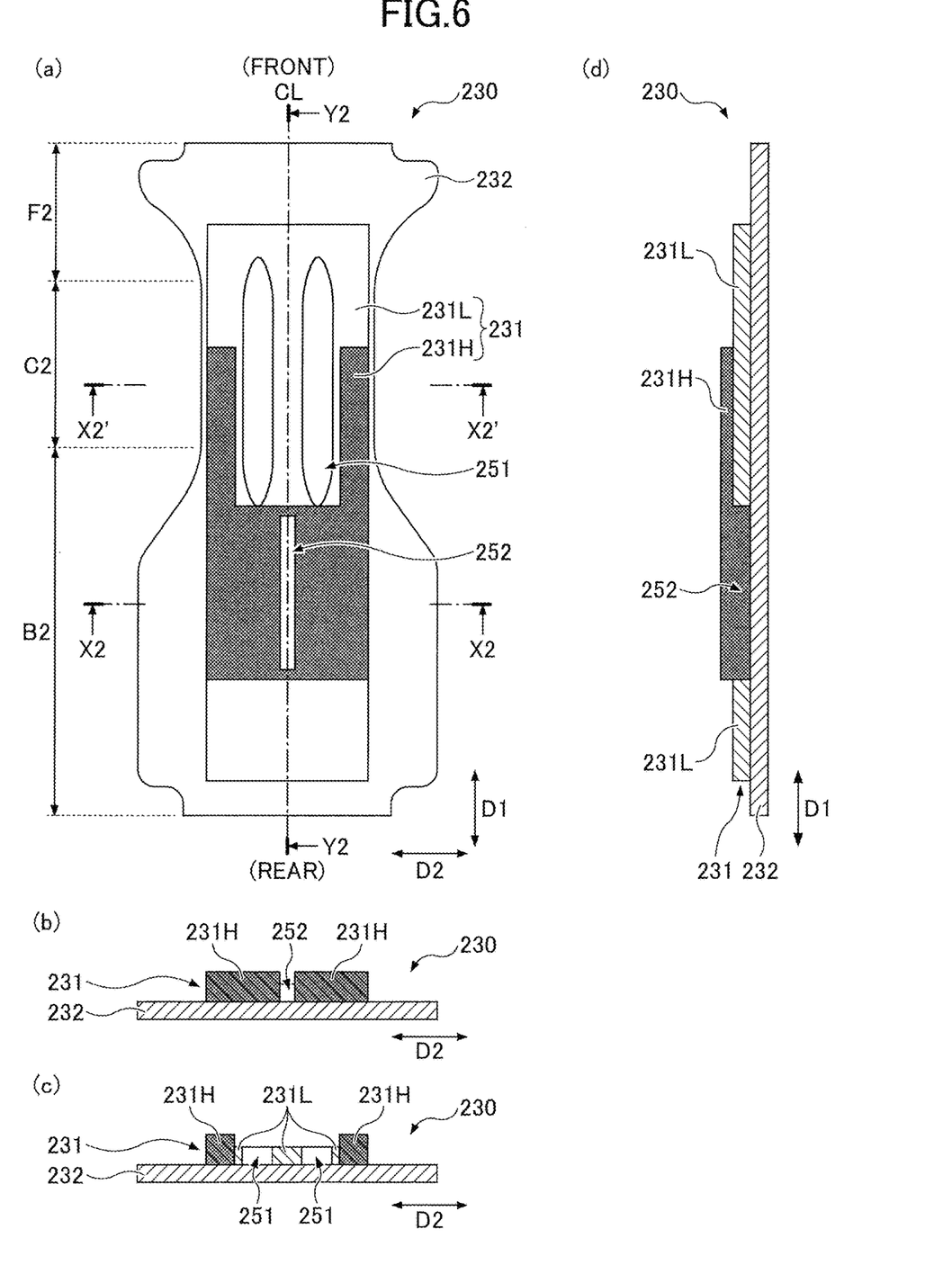
FIG. 6 is a diagram illustrating the absorber according to a second embodiment of the present invention.

In the embodiment illustrated in FIG. 3, a width of the high-stiffness part 131H (a distance from the edge portion of the groove 150 to the outer side along the width direction D2, that is, the width of the high-stiffness part 131H formed on one side of the groove 150) is approximately the same as the width of the groove 150, but the width of the high-stiffness part 131H may be greater than or smaller than the width of the groove 150. However, from the viewpoint of improving the effect of preventing the groove 150 from collapsing, the width of the high-stiffness part 131H is preferably greater than or equal to one-half the width of the groove 150. For example, the high-stiffness part 131H may extend beyond a position that is separated from the center line CL in the front-to-rear direction by $\frac{1}{3}$, $\frac{1}{2}$, and $\frac{2}{3}$ of one-half the width of the first absorber layer 131 (a length from the center line CL in the front-to-rear direction to an end edge of the first absorber layer 131 in the width direction D2). In addition, the high-stiffness part 131H may extend to the end edge of the first absorber layer 131 in the width direction D2 (FIG. 6).

More particularly, a width w of the high-stiffness part 131H (the distance from the edge portion of the groove 150 to the outer side along the width direction D2, that is, the width of the high-stiffness part 131H formed on one side of the groove 150) may be 15 mm to 75 mm. Further, when viewed in the width direction D2, a total width of the high-stiffness part 131H may be 30 mm to 150 mm.

The total width of the high-stiffness part 131H is preferably 10% to 60% of the width of the absorber 130. The effect of preventing the groove 150 from collapsing can be improved in a case where the total width of the high-stiffness part 131H is 10% or more of the width of the absorber 130, and it is possible to prevent the first absorber layer 131 from becoming too stiff in a case where the total width of the high-stiffness part 131H is 60% or less of the width of the absorber 130.

In addition, in the top view, a total area of the high-stiffness part 131H with respect to the area of the first absorber layer 131 is preferably 10% to 60%. The effect of preventing the groove 150 from collapsing can be improved in a case where the total area of the high-stiffness part 131H is 10% or more of the area of the absorber 130, and it is possible to reduce the exposure of the upper side of the high-stiffness part, and reduce discomfort or the like when the absorbent article is worn, in a case where the total area of the high-stiffness part 131H is 60% or less of the area of the absorber 130.

A depth of the groove 150 is not particularly limited as long as the groove 150 is formed from the upper side to the lower side. However, as illustrated in FIG. 3(b) and FIG. 3(c), the groove 150 preferably penetrates the upper first absorber layer 131 and reaches the lower second absorber layer 132, that is, an upper surface of the second absorber layer 132 preferably reaches a bottom surface of the groove 150.

In the case where the groove 150 reaches the lower second absorber layer 132, the body fluid can make direct contact with the second absorber layer 132, and thus, the body fluid is also absorbed by the second absorber layer 132, and is transferred in an in-plane direction inside the second absorber layer 132. As will be described later, such an effect becomes particularly conspicuous when the high-stiffness part 131H is configured as a high-density portion and the low-stiffness part 131L is configured as a low-density portion.

Figure 4:
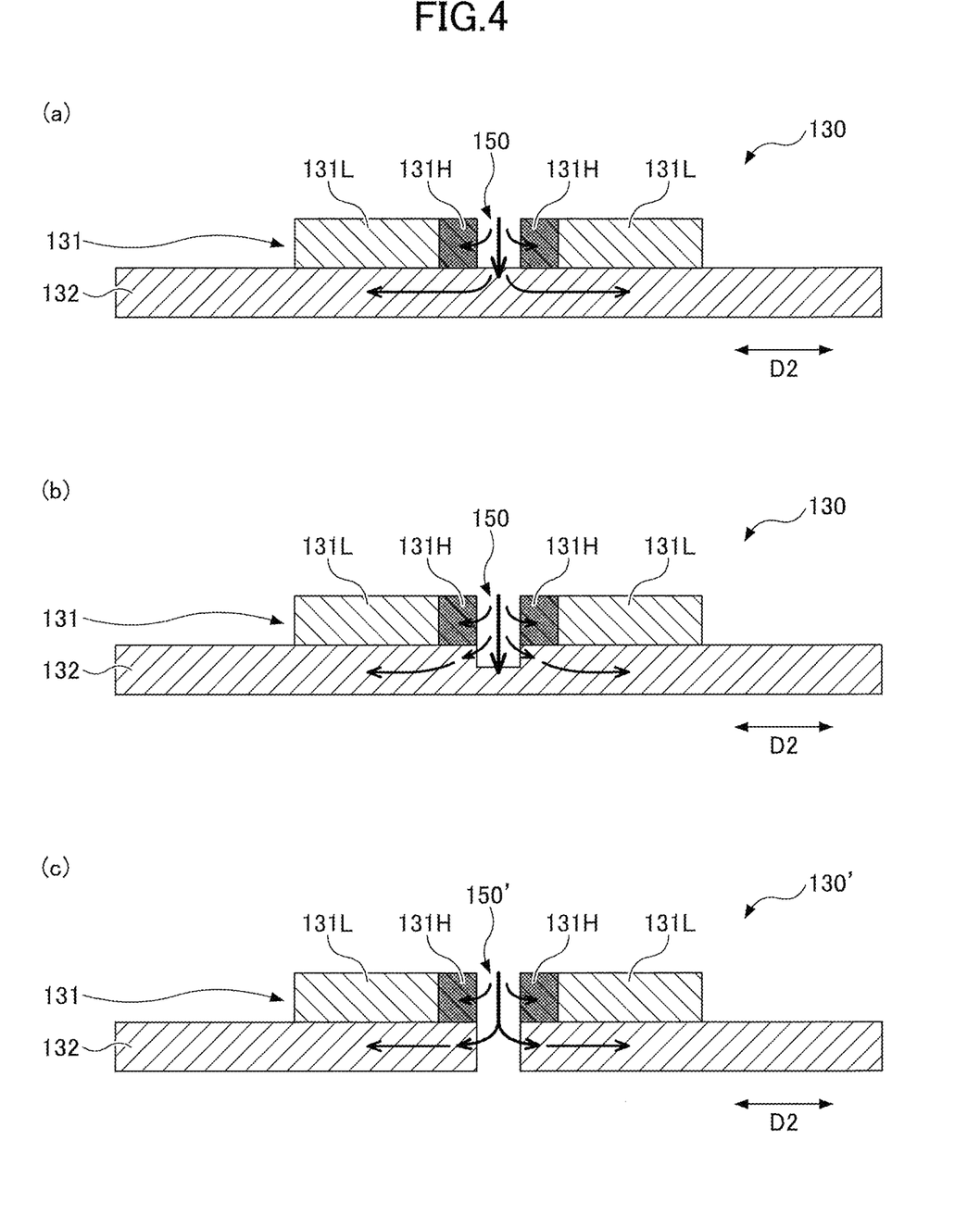
FIG. 4 is a schematic diagram illustrating a process in which body fluid is transferred in the absorber.

FIG. 4(a) schematically illustrates the transfer of the body fluid in absorber 130. As illustrated in FIG. 3(b) and FIG. 4(a), in this embodiment, a wall portion of the groove 150 is formed by the high-stiffness part 131H of the first absorber layer 131, and a bottom portion of the groove 150 is formed by the second absorber layer 132. For this reason, the body fluid that enters the groove 150 is drawn in toward the side of the high-stiffness part 131H of the first absorber layer 131, and may also be absorbed from the upper surface of the second absorber layer 132. Since the second absorber layer 132 has a relatively low stiffness and the body fluid can easily diffuse inside the second absorber layer 132, the body fluid absorbed from the upper surface of the second absorber layer 132 can quickly diffuse in the width direction D2 inside the second absorber layer 132 (FIG. 4(a)). Hence, because the diffusion is promoted in the absorber layer on the side further away from the skin in a state where the absorbent article is worn, it is possible to reduce a reverse flow of the body fluid.

Moreover, the second absorber layer 132 may have a cavity extending downward, and this cavity portion may form a part of the groove 150. In other words, as illustrated in FIG. 4(b), the wall portion of the groove 150 may be formed by the high-stiffness part 131H of the first absorber layer 131, and a portion of the second absorber layer 132, and the bottom portion of the groove 150 may be formed by a bottom portion of the cavity portion of the second absorber layer 132. According to this embodiment, it is also possible to obtain a diffusibility improving effect similar to that described above, because the body fluid entering the groove 150 makes contact with the second absorber layer 132 and may be absorbed directly from the second absorber layer 132 (FIG. 4(b)).

Furthermore, the absorber 130 may be provided with a slit 150' that penetrates both the first absorber layer 131 and the second absorber layer 132, in place of the groove 150 described above. FIG. 4(c) illustrates an absorber 130' provided with the slit 150'.

As illustrated in FIG. 4(c), a wall portion of the slit 150' is formed by the high-stiffness part 131H of the first absorber layer 131, and the second absorber layer 132. For this reason, the body fluid entering the slit 150' is drawn toward the side of the high-stiffness part 131H of the first absorber layer 131, and also absorbed toward the side of the second absorber layer 132. Thus, since the body fluid is directly absorbed by the second absorber layer 132, it is possible to quickly diffuse the body fluid in the width direction D2 inside the second absorber layer 132.

Accordingly, because an inner surface of the groove 150 is formed at least in part by the surface of the second absorber layer 132 having the relatively low stiffness, it is possible to improve the diffusibility of the body fluid inside the absorber 130.

The high-stiffness part 131H may be formed by increasing the density compared to the density of the surrounding regions. In other words, the high-stiffness part 131H may be configured as the high-density portion, and the low-stiffness part 131L may be configured as the low-density portion.

When the high-stiffness part 131H is configured as the high-density portion, the density thereof is preferably 20 $kg/m^3$ to 80 $kg/m^3$, and more preferably 30 $kg/m^3$ to 60 $kg/m^3$. In addition, the density of the low-stiffness part 131L is preferably 5 $kg/m^3$ to 40 $kg/m^3$, and more preferably 10 $kg/m^3$ to 30 $kg/m^3$. Furthermore, the density of the second absorber layer 132 is preferably 5 $kg/m^3$ to 40 $kg/m^3$, and more preferably 10 $kg/m^3$ to 30 $kg/m^3$.

The density of the low-stiffness part 131L and the density of the second absorber layer 132 may be the same or different. In a case where the density of the lower second absorber layer 132 is greater than the density of the low-density portion 131L of the upper first absorber layer 131, a force that draws the body fluid from the low-density portion 131L to the second absorber layer 132 may be generated at a portion where the low-density portion 131L and the second absorber layer 132 make close contact, and thus, this is preferable from a viewpoint of quickly transferring the body fluid downward and prevent the body fluid from remaining on the upper surface of the absorber.

A thickness of the entire absorber 30 (the thickness of the portion of the absorber 30 excluding the portion formed with the grooves) may be approximately 1 to approximately 30 mm, and preferably approximately 5 mm to approximately 25 mm. A thickness of the first absorber layer 131 may be approximately 5 mm to approximately 25 mm, and a thickness of the second absorber layer 132 may be approximately 5 mm to approximately 25 mm. When the thickness of the first absorber layer 131 is greater than the thickness of the second absorber layer 132, the amount of absorption increases on the side closer to the skin surface, and the reverse flow of the body fluid is reduced, and this is preferable in that the discomfort to the wearer can be reduced. The thickness of each of the first absorber layer 131 and the second absorber layer may be uniform throughout the in-plane direction, or the surface of each of the first absorber layer 131 and the second absorber layer may include slight irregularities.

In this specification, the density or the like of the absorber can be measured in the following manner. That is, a portion to be measured is cut out with an arbitrary size from the absorber, and the area and weight of the cut portion are measured. On the other hand, a thickness of the cut portion is measured using a thickness gauge ("Peacock", model number: FFD-7 manufactured by OZAKI MFG. CO., LTD.), for example. The density can be computed from the area, the thickness, and the weight that are measured as described above.

Figure 5:
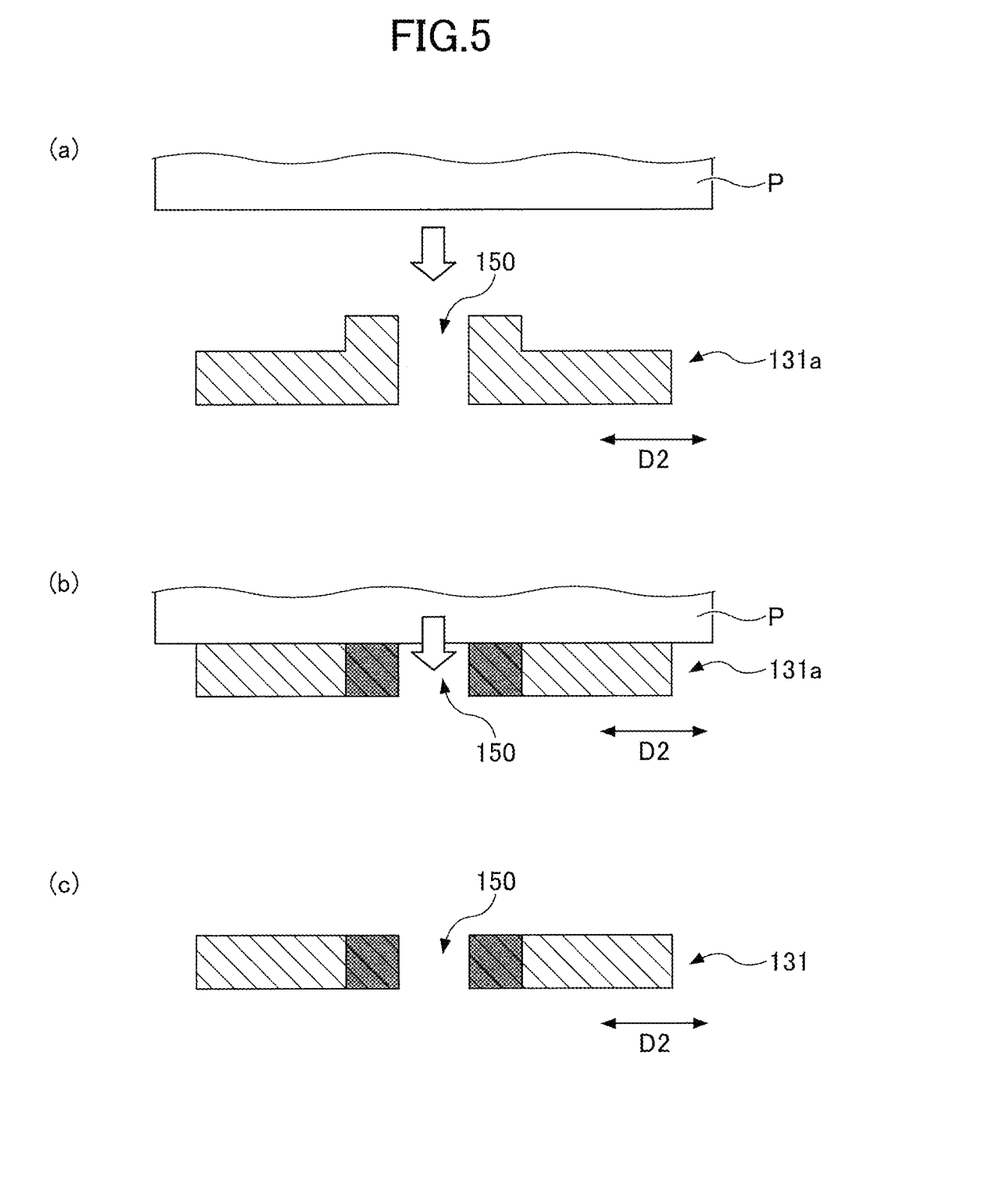
FIG. 5 is a diagram for explaining fabrication of a first absorber layer.

FIG. 5 illustrates an example of a method for fabricating the first absorber layer 131. First, as illustrated in FIG. 5(a), a fiber pile 131a formed with the groove 150 and having a shape such that a predetermined portion (a portion where the high-stiffness part 131H is to be formed) extending outward from the edge portion of the groove 150 in the width direction D2 has an increased thickness, is obtained. Next, as illustrated in FIG. 5(b), the fiber pile that is obtained is compressed of a pressing machine or the like using a mold P, so that the first absorber layer 131 is obtained (FIG. 5(c)). The thickness after compression may be uniform as illustrated in FIG. 5(c), or the thickness of the high-stiffness part 131H may be greater than the thickness of the low-stiffness part 131L.

In FIG. 5(a), the fiber pile 131a having the stepped portion is used, and the thickness of the portion that becomes the high-stiffness part 131H is uniform. However, it is possible to use the fiber pile 131a in which the thickness of the portion that becomes the high-stiffness part 131H gradually decreases from the edge portion of the groove 150 toward the outer side in the width direction D2, that is, the upper surface slopes downward toward the outer side in the width direction D2. In this case, it is possible to obtain an absorber in which the density of the high-stiffness part 131H of the first absorber layer 131 gradually decreases toward the outer side in the width direction D2.

The method for fabricating the high-stiffness part 131H is not limited to the method described above. For example, the high-stiffness part 131H and the low-stiffness part 131L may be fabricated, respectively, and the two portions may be arranged or bonded adjacent to each other, to form the first absorber layer 131. In addition, instead of fabricating the high-stiffness part 131H by increasing the density thereof, a material capable of increasing the stiffness may be used, for example, and the high-stiffness part 131H may be fabricated by changing the fiber material to a high-stiffness fiber material, or adding a high-stiffness material to the fiber material. Moreover, the high-stiffness part 131H and the low-stiffness part 131L may be fabricated by making both the density and the material of the two portions different.

The absorber 130 may be fabricated by laminating the first absorber layer 131 that is fabricated on the second absorber layer 132 that is separately fabricated. In this case, even when the stiffness of the second absorber layer 132 is not uniform within the layer, the density of the portion of the second absorber layer 132, provided under the high-stiffness part 131H of the first absorber layer 131, is configured to be lower than the stiffness of the high-stiffness part 131H. Both of the two laminated layers are preferably pressed in the thickness direction. According to such a two-layer structure, it is possible to obtain the absorber 130 that is sufficiently flexible, while preventing the grooves from collapsing.

The first absorber layer 131 and the second absorber layer 132 may be separate bodies, or may be integrally formed. When integrally forming the first absorber layer 131 and the second absorber layer 132, the absorber 130 may be obtained by fabricating a portion forming the first absorber layer 131, and thereafter laminating a material forming the second absorber layer 132 on the portion forming the first absorber layer 131, to form the second absorber layer 132 by further pressing or the like.

When the high-stiffness part 131H is configured as the high-density portion, the body fluid is easily drawn from the low-density region around the high-stiffness part 131H due to the difference in capillary forces. For this reason, when the first absorber layer 131 and the second absorber layer 132 are integrally formed, the body fluid that is once absorbed by the second absorber layer 132 is easily drawn upward toward the high-stiffness part 131H of the first absorber layer 131, and there is a possibility of the body fluid flowing back to the side closer to the top sheet. On the other hand, when the first absorber layer 131 and the second absorber layer 132 are formed as separate bodies, the body fluid can be prevented from flowing back to the side closer to the top sheet, because the drawing of the body fluid from the second absorber layer 132 to the first absorber layer 131, that is, to the side closer to the top sheet, can be reduced.

FIG. 6 illustrates an absorber 230 according to a second embodiment of the present invention. FIG. 6(a) illustrates a top view (viewed from the side closer to the top sheet) of the absorber 230, FIG. 6(b) illustrates a cross sectional view of along a line X2-X2 in FIG. 6(a), FIG. 6(c) illustrates a cross sectional view along a line X2'-X2' in FIG. 6(a), and FIG. 6(d) illustrates a cross sectional view of along a line Y2-Y2 in FIG. 6(a).

Similar to the other absorber 130 (first embodiment) described above, the absorber 230 is formed by laminating a first absorber layer 231 and a second absorber layer 232. However, the absorber 230 differs from the absorber 130 in that a plurality of grooves are formed therein, and the structure of the first absorber layer 231 differs from that of the absorber 130.

The grooves provided in the absorber 230 include a plurality of grooves that are independent of each other at the front and rear. More particularly, the grooves include two grooves 251 and 251 formed mainly in the crotch corresponding region C2, and one groove 252 formed mainly in the buttocks corresponding region (rear region) B2.

The one groove 252 provided mainly in the buttocks corresponding region B2, is located within the buttocks corresponding region B2, but may extend beyond the front end of the buttocks corresponding region B2. In the case where the groove 252 is located within the buttocks corresponding region B2, the length of the groove 252 is preferably 30% or more of the length of the buttocks corresponding region B2 in the front-to-rear direction D1, and is preferably 100 mm or greater.

The groove 252 is provided on the center line CL in the front-to-rear direction, but does not necessarily have to be provided on the center line CL in the front-to-rear direction. For example, a plurality of grooves may be formed mainly in the buttocks corresponding region B2, and the plurality of grooves may be spaced apart from each other on both sides of center line CL in the front-to-rear direction. However, even in this case, the groove 252 is preferably provided at the center along the width direction D2 (a region having the center line CL in the front-to-rear direction as a center line thereof, and having a width that is one-half the width of the absorber) when the position where the body fluid is excreted and permeates into the absorber is taken into consideration.

The grooves 251 and 251, provided mainly in the crotch corresponding region C2, are arranged at positions spaced apart from each other on both sides of the center line CL in the front-to-rear direction. The grooves 251 and 251 are provided beyond the front and rear ends of the crotch corresponding region C2, respectively, but does not necessarily have to extend beyond one of the front and rear ends of the crotch corresponding region C2, or may be arranged within the crotch corresponding region C2.

A width of each of the grooves 251 and 251 is greater than the width of the groove 252 provided in the buttocks corresponding region B2, but the relationship between the width of the groove 251 and the width of the groove 252 is not particularly limited. However, the width of the grooves 251 and 251 is preferably set large, since it becomes possible to improve the air permeability of the crotch corresponding region C2 where the body fluid easily stagnates. In place of the two grooves 251 and 251, a single groove, arranged in the crotch corresponding region C2, may be provided on the center line CL in the front-to-rear direction.

As illustrated in FIG. 6(a) and FIG. 6(b), a high-stiffness part 231H is provided at an edge portion on a side of the groove 252 in the buttocks corresponding region B2, toward an outer side of the edge portion in the width direction D2. In other words, the groove 252 is reinforced at the side by the high-stiffness part 231H. Hence, the function of the groove can be maintained in the buttocks corresponding region B2 where the pressure is easily applied in the thickness direction. In this embodiment, the high-stiffness part 231H extends from the edge portion of the groove 252 to the side edge of the first absorber layer 231. For this reason, the effect of reinforcing the groove 252 is large.

Moreover, in the embodiment (second embodiment) of FIG. 6, the high-stiffness part 231H extends from the front end and the rear end of the groove 252 in the front-to-rear direction D1, and is continuously provided to surround the entire groove 252. As described in the embodiment (first embodiment) of FIG. 3, this embodiment is preferable from a viewpoint of easily maintaining the original shape of the groove even when the absorber is receives a force from the side or the like, but the high-stiffness part 231H may not be arranged, and the low-stiffness part 231L may be arranged instead, in at least one of the front edge portion and the rear edge portion of the groove 252.

In the embodiment illustrated in FIG. 6, the high-stiffness part 231H is not provided at the edge portion on the side of the grooves 251 and 251, and the low-stiffness part 231L, having a stiffness lower than that of the high-stiffness part 231H, extends from the edge portion of the grooves 251 and 251 toward the outer side in the width direction D2. Since the crotch corresponding region C2 easily adheres to the wearer's skin when the absorbent article is worn, the provision of the low-stiffness part 231L at the edge portion of the grooves 251 and 251 is preferable from a view point of improving the flexibility of the absorber and the comfort when the absorbent article worn.

On the other hand, the high-stiffness part 231H may also be provided at the edge portion on the side of the grooves 251 and 251, to reinforce the grooves 251 and 251. For example, in a case where the wearer lies sideways and closes the legs, or the like in a state where the absorber 230 is folded into two parts in the width direction D2 near the center line CL in the front-to-rear direction, a force is easily applied in the thickness direction even in the crotch corresponding region C2. In this case, when the high-stiffness part 231H is provided at the edge portion on the side of the grooves 251 and 251 in the crotch corresponding region C2, it is possible to prevent the width of the grooves from narrowing, or the grooves from closing.

In addition, the high-stiffness part 231H is not provided at the edge portion in the front of the grooves 251 and 251, and the low-stiffness part 231L extends to the front end of the first absorber layer 231. For this reason, it is possible to secure flexibility from the crotch corresponding region C2 to the front region F2, that is, in the regions where the absorber easily adheres to the skin.

On the other hand, the edge portion in the rear of the grooves 251 and 251 make contact with the high-stiffness part 231H. In the case where the high-stiffness part 231H is formed by the high-density portion, this is preferable in that the body fluid guided rearward along the grooves 251 and 251 can easily be drawn into the high-stiffness part 231H making contact with the edge portion in the rear of the grooves 251 and 251. However, the high-stiffness part 231H may be provided at the edge portion in the front of the grooves 251 and 251, and the low-stiffness part 231L may be provided at the edge portion in the rear of the grooves 251 and 251.

In the embodiment illustrated in FIG. 6, the length of the high-stiffness part 231H in the front-to-rear direction D1 is longer on both side portions of the first absorber layer 231 than at a central portion of the first absorber layer 231. More particularly, the high-stiffness part 231H extends in front on both side portions of the first absorber layer 231, frontward beyond the front end of the buttocks corresponding region B2 (FIG. 6(a) and FIG. 6(c)). Hence, the stiffness on both side portions of the first absorber layer 231 can be increased in a portion of the crotch corresponding region C2. Since the side portions of the crotch corresponding region C2 is susceptible to a force particularly from the side, an appropriate worn state of the absorbent article can be maintained for a long time, by at least partially increasing the stiffness of these side portions, without causing the absorber in the crotch corresponding region C2 from becoming twisted.

In this embodiment, a thickness of the high-stiffness part 231H is greater than a thickness of the low-stiffness part 231L (FIG. 6(d)). A relationship of the thicknesses of each of the portions is not limited to the embodiment illustrated in FIG. 6, and the thickness of the high-stiffness part 231H and the thickness of the low-stiffness part 231L may be the same. However, because a height of the high-stiffness part 231H reinforcing the groove 252 is higher than other portions, the amount of absorbent material in the buttocks corresponding region B2 and can be increased, and the depth of the groove 252 can be increased. Preferably, the thickness of the high-stiffness part 231H is 1 mm to 5 mm greater than the thickness of the low-stiffness part 231L.

As described above, the high-stiffness part 231H extends in front on both side portions of the first absorber layer 231. In other words, the high-stiffness part 231H is arranged to surround the grooves 251 and 251 formed in the crotch corresponding region C2, from the rear and from the sides (FIG. 6(a)). In the case where the thickness of the high-stiffness part 231H is greater than the thickness of the low-stiffness part 231L, a stepped portion is formed at portions other than the portion provided with the groove 252, when viewed in the front-to-rear direction D1. Accordingly, the body fluid that moved from the front to the rear can quickly be guided to the groove 252 at the rear along a front contour of the high-stiffness part 231H. As a result, it is possible to effectively prevent a leakage of the body fluid to the side (outer side in the width direction D2).

Figure 7:
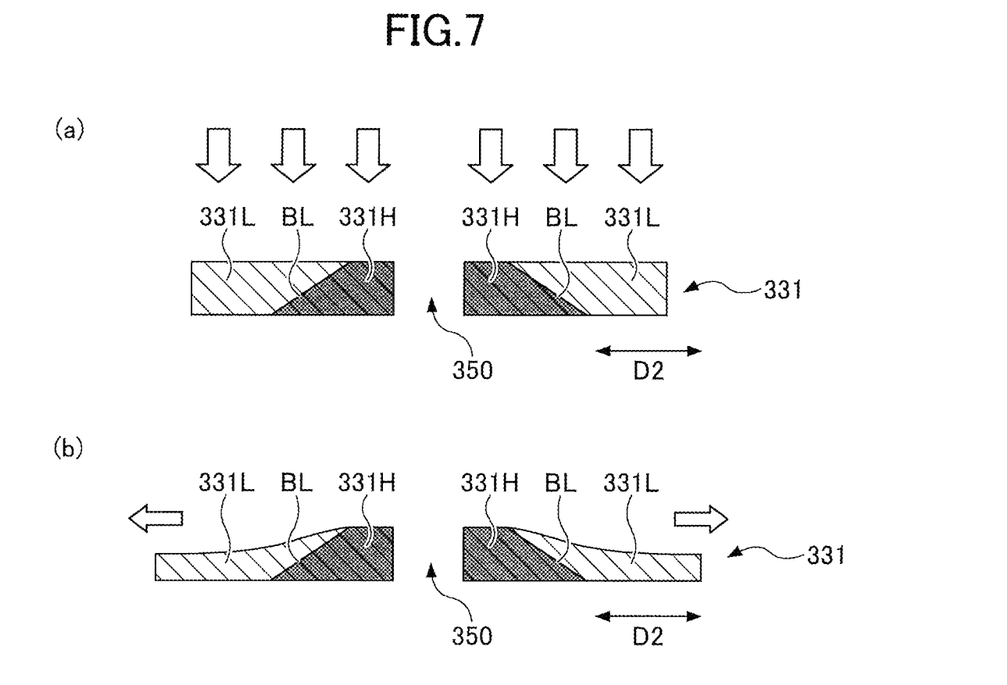
FIG. 7 is a diagram illustrating the absorber according to a third embodiment of the present invention.

FIG. 7(a) illustrates a third embodiment of the present invention. FIG. 7(a) illustrates a cross section of only the first absorbent layer 331 of the absorber included in the absorbent article. This cross section corresponds to a cross section of the absorber cut along the width direction D2, that is, the cross section corresponding to a portion (upper layer) of the cross section of FIG. 3(b).

Similar to the first absorber layer 131 of the absorber 130 (first embodiment), a first absorber layer 331 according to the third embodiment includes a high-stiffness part 331H extending to an outer side from an edge portion of a groove 350 in the width direction D2, thereby reinforcing the groove 350. In addition, a low-stiffness part 331L having a stiffness lower than that of the high-stiffness part 331H is provided on an outer side of the high-stiffness part 331H in the width direction D2. However, the first absorber layer 331 differs from the first absorber layer 131 (first embodiment) in that a width of the high-stiffness part 331H on the lower side (the side closer to the back sheet) is greater than the width on the upper side (the side closer to the top sheet).

According to this embodiment, the region of the high-stiffness part 331H exposed on side closer to the top sheet can be reduced without changing a volume of the high-stiffness part 331H. Hence, it is possible to reduce the stiff portion that may adhere to the skin when the absorbent article is worn, while securing the above described function of the high-stiffness part that prevents the groove or slit from collapsing, and thus, comfortableness can be achieved when the absorbent article is worn.

The width of the high-stiffness part 331H may increase gradually, or in steps, toward the lower side in the thickness direction, but as illustrated in FIG. 7(a), the width of the high-stiffness part 331H preferably increases gradually toward the lower side. More particularly, in this embodiment, a boundary line BL between the high-stiffness part 331H and the low-stiffness part 331L viewed in the cross section is inclined toward the center line CL in the front-to-rear direction. In other words, in a view of the entire first absorber layer 331, the boundary line BL fans out (when viewed in the thickness direction, extends more toward the outer side in the width direction D2, the more toward the side closer to the back sheet 21).

When a force is applied to the first absorber layer 331 illustrated in FIG. 7(a) in the thickness direction from the side close to the skin, for example, the high-stiffness part 331H is not easily deformed, but the low-stiffness part 331L may be compressed and deformed. In this case, the low-stiffness part 331L is pushed toward the lower side (the side closer to the back sheet) along the slope of the boundary line BL, and is also pushed toward the outer side in the width direction D2, and may expand toward the outer side in the width direction D2 (FIG. 7(b)). Hence, the high-stiffness part 331H may be compressed to have a gentle slope without generating a stepped portion between the high-stiffness part 331H and the low-stiffness part 331L. For this reason, even when a large force is exerted from the buttocks near the groove 350, for example, it is possible to reduce the discomfort caused by the absorber after the deformation (after the compression) making contact with the skin.

Although a pad type disposable diaper is described with reference to specific embodiments, the embodiments may be applied to other forms of disposable diapers, such as the tape type, the pants type, or the like, as well as to sanitary napkins.

Hereinafter, preferred embodiments of the present invention will be described below.

Appended Clause 1

An embodiment in accordance with appended clause 1 relates to an absorbent article comprising a liquid permeable top sheet, a liquid impermeable back sheet, and an absorber provided between the two sheets, the absorbent article having a predetermined length in a front-to-rear direction, and a predetermined width in a width direction perpendicular to the front-to-rear direction, wherein the absorber is provided with a groove or a slit extending in the front-to-rear direction, the absorber includes a first absorber layer on the side closer to the top sheet, and a second absorber layer on the side closer to the back sheet, and the first absorber layer includes a high-stiffness part extending outward in the width direction from an edge portion of the groove or slit, and a stiffness of the high-stiffness part is higher than a stiffness of the second absorber layer.

According to the embodiment in accordance with appended clause 1 described above, since the groove or the slit extending in the front-to-rear direction is provided in the absorber, it is possible to promote diffusion of the body fluid in the front-to-rear direction. In addition, since the absorber has the first absorber layer on the side closer to the top sheet, and the second absorber layer on the side closer to the back sheet, and the first absorber layer has the high-stiffness part that extends outward from the edge portion of the groove or the slit in the width direction, the groove or the slit is reinforced and prevented from collapsing.

Further, the stiffness of the high-stiffness part is higher than the stiffness of the second absorber layer laminated underneath. In other words, in the region where the high-stiffness part is provided, the second absorber layer having the stiffness lower than the stiffness of the high-stiffness part is provided on the side (the lower side) closer to the back sheet. For this reason, it is possible to improve the flexibility of the entire absorber, while securing the effect of the high-stiffness part of the first absorber layer, which prevents the groove or the slit from collapsing.

Appended Clause 2

In an embodiment in accordance with appended clause 2, the absorber is provided with a groove reaching the second absorber layer, or a slit penetrating the first absorber layer and the second absorber layer.

According to the embodiment in accordance with appended clause 2 described above, the groove or slit provided in the absorber is the groove that reaches the second absorber layer on the side closer to the back sheet, or the slit that penetrates the first absorber layer and the second absorber layer. According to this structure, a portion of the wall portion of the groove or the slit is formed by the second absorber layer of relatively low stiffness. Hence, the body fluid that moves along the groove or the slit is absorbed from the second absorber layer on the side closer to the back sheet, and is also diffused to the outer side in the width direction, thereby improving the diffusibility in the in-plane direction inside the absorber.

Appended Clause 3

In an embodiment in accordance with appended clause 3, a sum of areas of the high-stiffness part in a top view is 5% to 50% of an area of the absorber.

According to the embodiment in accordance with appended clause 3 described above, because the high-stiffness part has a predetermined area, the groove or the slit is prevented from collapsing, and the area of the region that makes contact with the skin can be made small, thereby reducing the discomfort when the absorbent article is worn.

Appended Clause 4

In an embodiment in accordance with appended clause 4, the first absorber layer includes a low-stiffness part, having a stiffness lower than the stiffness of the high-stiffness part, provided on an outer side of the high-stiffness part in the width direction, and the width of the high-stiffness part is greater on the side closer to the back sheet.

According to the embodiment in accordance with appended clause 4 described above, the low-stiffness part is provided on the outer side of the high-stiffness part in the width direction, and the width of the high-stiffness part is wider on the side closer to the back sheet. For this reason, it is possible to reduce the area of the high-stiffness part exposed on the side closer to the top sheet, without changing the volume of the high-stiffness part. Hence, it is possible to reduce the stiff portion that may make contact with the skin when the absorbent article is worn, while securing the above described function of the high-stiffness part function, which prevents the groove or the slit from collapsing, and thus, comfortableness can be achieved when the absorbent article is worn.

Appended Clause 5

In an embodiment in accordance with appended clause 5, the high-stiffness part is provided at least in a buttocks corresponding region corresponding to buttocks of a wearer when the absorbent article is worn.

According to the embodiment in accordance with appended clause 5 described above, the high-stiffness part that reinforces the groove or the slit is provided at least in the buttocks corresponding region. The absorber in the buttocks corresponding region is particularly susceptible to a force in the thickness direction, so the groove or the slits in the buttocks corresponding region may easily collapse. However, this embodiment positively prevents the groove or the slit from collapsing in the buttocks corresponding region, and effectively prevents deterioration of the original function of the groove or the slit.

Appended Clause 6

In an embodiment in accordance with appended clause 6, a low-stiffness part having a stiffness lower than the stiffness of the high-stiffness part, extends outward from the edge portion of the groove or slit in the width direction, in a region in front of the buttocks corresponding region.

According to the embodiment in accordance with appended clause 6 described above, the low-stiffness part extends outward from the groove or the slit in the width direction in front of the buttocks corresponding region. The absorber in the region adjacent to and in front of the buttocks corresponding region is less likely to receive a force in the thickness direction when compared to the buttocks corresponding region, but the absorber may easily make contact with the skin when the absorbent article is worn. Accordingly, this embodiment prioritizes securing the flexibility of the absorber in front of the buttocks corresponding region, and can improve the comfort when the absorbent article is worn.

This application claims priority to Japanese Patent Application No. 2018-106939, filed Jun. 4, 2018, the entire contents of which are hereby incorporated by reference.

DESCRIPTION OF THE REFERENCE NUMERALS

1 Absorbent article
21 Back sheet
22 Top sheet
24 Gather sheet
25 Intermediate sheet
26 Packaging sheet
30, 130, 230, 330 Absorber
131, 231, 331 First absorber layer
131H, 231H, 331H High-stiffness part
131L, 231L, 331L Low-stiffness part
132, 232, 332 Second absorber layer
150, 250, 251, 252, 350 Groove
150' Slit
F1 Front region (of absorbent article)
F2 Front region (of absorber)
C1 Crotch corresponding region (of absorbent article)
C2 Crotch corresponding region (of absorber)
B1 Rear region or buttocks corresponding region (of absorbent article)
B2 Rear region or buttocks corresponding region (of absorber)
BL Boundary between the high-stiffness part and the low-stiffness part
CL Center line in front-to-rear direction (center line along first direction D1)
D1 Front-to-rear direction (first direction)
D2 Width direction (second direction)
G Gather
P Mold of pressing machine
Q Fluid excretion orifice corresponding portion

The invention claimed is:

1. An absorbent article comprising:
a liquid-permeable top sheet;
a liquid-impermeable back sheet; and
an absorber provided between the top sheet and the back sheet, wherein
the absorbent article has a predetermined length in a front-to-rear direction, and a predetermined width in a width direction perpendicular to the front-to-rear direction,
the absorber includes a first absorber layer located at a position closer to the top sheet than to the back sheet, a second absorber layer located at a position closer to the back sheet than to the top sheet, and a groove or a slit formed in the first absorber layer and extending in the front-to-rear direction,
the first absorber layer includes
a high-stiffness part, made of an absorbent material, and extending outward in the width direction from an edge portion of the groove or slit, and
a low-stiffness part, made of an absorbent material, having a stiffness lower than a stiffness of the high-stiffness part, and provided on an outer side of the high-stiffness part in the width direction,
an entirety of the first absorber layer, including the high-stiffness part and the low-stiffness part, overlaps the second absorber layer in a top view, and
the stiffness of the high-stiffness part is higher than a stiffness of the second absorber layer.

2. The absorbent article as claimed in claim 1, wherein the groove is configured to reach the second absorber layer, or the slit is configured to penetrate the first absorber layer and the second absorber layer.

3. The absorbent article as claimed in claim 2, wherein a sum of areas of the high-stiffness part in a top view is 5% to 50% of an area of the absorber.

4. The absorbent article as claimed in claim 2, wherein a width of the high-stiffness part at a position closer to the back sheet than to the top sheet is greater than a width of the high-stiffness part at a position closer to the top sheet than to the back sheet.

5. The absorbent article as claimed in claim 2, wherein the high-stiffness part is provided at least in a buttocks corresponding region corresponding to buttocks of a wearer when the absorbent article is worn.

6. The absorbent article as claimed in claim 5, wherein the low-stiffness part extends outward from the edge portion of the groove or slit in the width direction, in a region in front of the buttocks corresponding region.

7. The absorbent article as claimed in claim 1, wherein a sum of areas of the high-stiffness part in a top view is 5% to 50% of an area of the absorber.

8. The absorbent article as claimed in claim 7, wherein a width of the high-stiffness part at a position closer to the back sheet than to the top sheet is greater than a width of the high-stiffness part at a position closer to the top sheet than to the back sheet.

9. The absorbent article as claimed in claim 7, wherein the high-stiffness part is provided at least in a buttocks corresponding region corresponding to buttocks of a wearer when the absorbent article is worn.

10. The absorbent article as claimed in claim 9, wherein the low-stiffness part extends outward from the edge portion of the groove or slit in the width direction, in a region in front of the buttocks corresponding region.

11. The absorbent article as claimed in claim 1, wherein a width of the high-stiffness part at a position closer to the back sheet than to the top sheet is greater than a width of the high-stiffness part at a position closer to the top sheet than to the back sheet.

12. The absorbent article as claimed in claim 11, wherein the high-stiffness part is provided at least in a buttocks corresponding region corresponding to buttocks of a wearer when the absorbent article is worn.

13. The absorbent article as claimed in claim 12, wherein the low-stiffness part extends outward from the edge portion of the groove or slit in the width direction, in a region in front of the buttocks corresponding region.

14. The absorbent article as claimed in claim 1, wherein the high-stiffness part is provided at least in a buttocks corresponding region corresponding to buttocks of a wearer when the absorbent article is worn.

15. The absorbent article as claimed in claim 14, wherein the low-stiffness part extends outward from the edge portion of the groove or slit in the width direction, in a region in front of the buttocks corresponding region.

16. The absorbent article as claimed in claim 1, wherein
the first absorber layer is laminated on the second absorber layer, so that the high-stiffness part and the low-stiffness part of the first absorber layer make contact with the second absorber layer, respectively, and
a width of the first absorber layer, including the high-stiffness part and the low-stiffness part, is smaller than a width of the second absorber layer in the width direction.

17. The absorbent article as claimed in claim 1, wherein the high-stiffness part surrounds the groove or slit in a top view.

18. The absorbent article as claimed in claim 1, wherein
the high-stiffness part partially overlaps the low-stiffness part, and
a portion of the high-stiffness part, partially overlapping the low-stiffness part, has a thickness greater than a thickness of the low-stiffness part.

19. The absorbent article as claimed in claim 1, wherein the high-stiffness part has a thickness greater than a thickness of the low-stiffness part.

20. The absorbent article as claimed in claim 1, further comprising:
an intermediate sheet, made of a material having a low water retention and a high liquid permeability, provided between the absorber and the top sheet, wherein
the first absorber layer is laminated on the second absorber layer, so that the high-stiffness part and the low-stiffness part of the first absorber layer make contact with the second absorber layer, respectively, and
the second absorber layer makes contact with the back sheet.

* * * * *